United States Patent [19]

Zergényi

[11] 4,294,966
[45] Oct. 13, 1981

[54] PROCESS FOR INVERTING THE CONFIGURATION IN OPTICALLY ACTIVE COMPOUNDS

[75] Inventor: Janos Zergényi, Seltisberg, Switzerland

[73] Assignee: Ciba-Geigy Corporation, Ardsley, N.Y.

[21] Appl. No.: 58,222

[22] Filed: Jul. 16, 1979

[30] Foreign Application Priority Data

Jul. 28, 1978 [CH] Switzerland ................. 8145/78

[51] Int. Cl.³ .................. C07D 239/24; C07D 241/10
[52] U.S. Cl. .................... 544/316; 544/318; 544/315; 544/408; 546/288; 546/300; 548/305; 548/337; 260/326.15; 260/326.5 R
[58] Field of Search ............... 260/570.5 CA, 570.7, 260/570.8, 326.15, 326.5 R; 544/318, 316, 315, 408; 546/288, 300; 548/337, 305

[56] References Cited

U.S. PATENT DOCUMENTS

2,446,192  8/1948  Pfister ........................ 260/534

FOREIGN PATENT DOCUMENTS

585164  9/1933  Fed. Rep. of Germany .

OTHER PUBLICATIONS

Nagai et al., "Liebigs Annalen der Chemie", 470, pp. 157–182 (1929).
"J. Am. Chem. Soc.", 70, pp. 2297–2298 (1948).
Chem. Abst. 84, 43593x (1976).
Müller "Liebigs Annalen der Chemie", 599, 211–221 (1956).

*Primary Examiner*—Nicholas S. Rizzo
*Attorney, Agent, or Firm*—Prabodh I. Almaula

[57] ABSTRACT

The invention relates to a process for inverting the configuration in optically active compounds of the formula

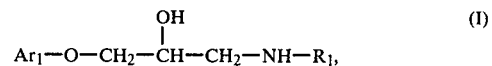

in which
  $Ar_1$ represents a monocyclic or polycyclic, carbocyclic or heterocyclic radical that has at least one ring of aromatic character and is bonded to the oxygen atom by way of a ring carbon atom, preferably of the ring of aromatic character, and
  $R_1$ represents an optionally substituted aliphatic, cycloaliphatic or araliphatic hydrocarbon radical, or the salts thereof, characterised in that an optically active compound of the formula

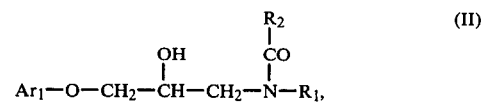

having a R(+) or S(−) configuration, in which
  $R_2$ represents a monocyclic or polycyclic, carbocyclic or heterocyclic radical, or an optionally substituted aliphatic, cycloaliphatic or araliphatic hydrocarbon radical, is converted, by treating with a strong oxygen-containing inorganic or organic acid or halides thereof, into an optically active compound of the formula

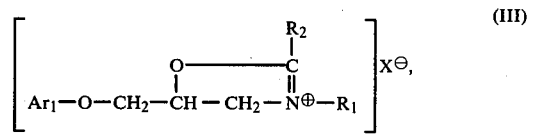

in which
  $X^{\ominus}$ represents the anion of a strong, oxygen-containing inorganic or organic acid or of a halogen atom and the resulting compound of the formula III is hydrolysed, optionally by way of the corresponding free base as intermediate, to form a compound of the formula I of a configuration opposite to that of the starting material used and, if desired, a free compound of the formula I is converted into a salt or a resulting salt is converted into the free compound.

1 Claim, No Drawings

PROCESS FOR INVERTING THE CONFIGURATION IN OPTICALLY ACTIVE COMPOUNDS

The invention relates to a process for inverting the configuration in optically active compounds of the formula

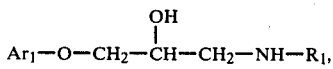

$$Ar_1-O-CH_2-\underset{\underset{OH}{|}}{CH}-CH_2-NH-R_1, \quad (I)$$

in which $Ar_1$ represents a monocyclic or polycyclic, carbocyclic or heterocyclic radical that has at least one ring of aromatic character and is bonded to the oxygen atom by way of a ring carbon atom, preferably of the ring of aromatic character, and $R_1$ represents an optionally substituted aliphatic, cycloaliphatic or araliphatic hydrocarbon radical, or the salts thereof, and new intermediates and salts thereof suitable for carrying out the process.

The configuration inversion according to the invention is concerned with the secondary alcohol group present in the group

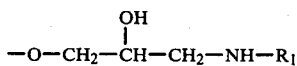

$$-O-CH_2-\underset{\underset{OH}{|}}{CH}-CH_2-NH-R_1$$

the spatial arrangement of this secondary alcohol group corresponding either to the $R(+)$ or $S(-)$ configuration.

Accordingly, in accordance with the process of the invention a compound of $R(+)$ configuration is converted into one of $S(-)$ configuration or a compound of $S(-)$ configuration is converted into one of $R(+)$ configuration. This configuration inversion causes a reversal of the direction of optical rotation.

Carbocyclic radicals $Ar_1$ of aromatic character are especially phenyl; optionally partially saturated, bicyclic, aromatic hydrocarbon radicals, such as naphthyl, for example 1-naphthyl or 2-naphthyl, 1,2,3,4-tetrahydrobenznaphthyl, for example 1,2,3,4-tetrahydro-5-naphthyl, benz-indenyl, for example 4-indenyl or 5-indenyl, or benz-indanyl, for example 4-indanyl or 5-indanyl; and optionally partially saturated polycyclic aromatic hydrocarbon radicals, such as benz-fluorenyl, for example 4-fluorenyl, or 9,10-ethano-9-10-dihydrobenz-anthryl, for example 9,10-ethano-9,10-dihydro-1-anthryl; wherein partially saturated radicals of the above kind are bonded to the oxygen atom by way of a ring carbon atom of the aromatic moiety.

Heterocyclic radicals $Ar_1$ contain as ring hetero atoms especially one or more ring nitrogen atoms and, preferably in addition to a ring nitrogen atom, also a ring oxygen or ring sulphur atom. Radicals of this type are especially monocyclic, five or six-membered, mono-, di- or tri-azacyclic radicals, especially monocyclic, monoazacyclic six-membered radicals of aromatic character, such as pyridyl, for example pyrid-2-yl, pyrid-3-yl or pyrid-4-yl; monocyclic, diazacyclic six-membered radicals of aromatic character, such as pyridazinyl, for example pyridazin-3-yl, pyrimidinyl, for example pyrimidin-2-yl or pyrimidin-4-yl, or pyrazinyl, for example pyrazin-2-yl; monocyclic, thiadiazacyclic five-membered radicals of aromatic character, such as thiadiazolyl, for example, 1,2,5-thiadiazol-3-yl; optionally partially saturated bicyclic, monoazacyclic radicals of aromatic character having a five or six-membered heterocyclic ring, such as indolyl, for example 4-indolyl, or optionally partially saturated quinolinyl, for example, 1,2,3,4-tetrahydroquinolin-5-yl; or bicyclic monothiacyclic radicals partially of aromatic character, such as 2H-thiochromenyl, for example 2H-thiochromen-8-yl.

The above radicals $Ar_1$ may be unsubstituted or substituted, $Ar_1$ containing especially one, but alternatively more, especially two, substituents. The latter are especially optionally substituted aliphatic or cycloaliphatic hydrocarbon radicals, optionally etherified or esterified hydroxy or mercapto groups, acyl radicals, optionally functionally modified carboxyl groups, nitro or optionally substituted amino groups. Saturated moieties of the group $Ar_1$ may contain apart from the above-mentioned substituents double-bonded substituents, especially oxo.

Aliphatic hydrocarbon radicals as substituents in the radical $Ar_1$ are especially lower alkyl, lower alkenyl, and also lower alkynyl. Substituents of such radicals, especially of lower alkyl and of lower alkenyl, are optionally etherified or esterified hydroxy or mercapto groups, for example lower alkoxy or lower alkylthio; halogen; optionally functionally modified carboxyl, especially optionally N-substituted, such as N-lower alkylated, carbamoyl; or optionally substituted amino, especially acylamino, wherein acyl is the radical of an organic carboxylic acid, of a semi-derivative of carbonic acid, or of an organic sulphonic acid, such as lower alkanoylamino, lower alkoxycarbonylamino, optionally N-substituted, such as N'-lower alkylated, ureido, for example ureido, N'-lower alkylureido or N',N'-di-lower alkylureido, or also lower alkylsulphonylamino. Substituted lower alkyl radicals are especially hydroxy-lower alkyl, lower alkoxy-lower alkyl, lower alkylthio-lower alkyl, halo-lower alkyl, optionally N-lower alkylated carbamoyl-lower alkyl, lower alkanoylamino-lower alkyl or lower alkoxycarbonylamino-lower alkyl, and substituted lower alkenyl radicals are especially lower alkanoylamino-lower alkenyl or lower alkoxycarbonylamino-lower alkenyl.

Cycloaliphatic hydrocarbon radicals are especially monocyclic or polycyclic cycloalkyl radicals.

Etherified hydroxy or mercapto groups as substituents in the radical $Ar_1$ are especially hydroxy or mercapto groups etherified by optionally substituted aliphatic hydrocarbon radicals, such as lower alkoxy or phenyl-lower alkoxy, lower alkenyloxy or lower alkynyloxy, and also tetrahydrofurfuryloxy, lower alkylthio or lower alkenylthio. Substituents of such etherifying aliphatic hydrocarbon radicals, especially of etherifying lower alkyl, are especially optionally etherified or esterified hydroxy or mercapto, such as lower alkoxy, lower alkylthio or halogen; or optionally substituted amino, such as acylamino, for example lower alkanoylamino or lower alkoxycarbonylamino. A hydroxy or mercapto group etherified by correspondingly substituted aliphatic hydrocarbon radicals is especially lower alkoxy-lower alkoxy, lower alkylthio-lower alkoxy or lower alkoxy-lower alkylthio, and also lower alkanoylamino-lower alkoxy or lower alkoxycarbonylamino-lower alkoxy.

Esterified hydroxy or mercapto groups as substituents in the groups $Ar_1$ are especially halogen and also lower alkanoyloxy.

Acyl groups as substituents in the radical $Ar_1$ are especially lower alkanoyl.

Optionally functionally modified carboxyl groups as substituents in $Ar_1$ are especially esterified or amidated carboxyl, and also cyano. Esterified carboxyl is especially lower alkoxycarbonyl, whereas amidated carboxyl is optionally substituted carbamoyl, such as carbamoyl, N-lower alkylcarbamoyl or N,N-di-lower alkylcarbamoyl.

Optionally substituted amino groups as substituents in the groups $Ar_1$ are especially acylamino, wherein acyl is especially the corresponding radical of an organic carboxylic acid or of a semi-derivative of carbonic acid, or also of an organic sulphonic acid, such as lower alkanoylamino, lower alkoxycarbonylamino or optionally N'-lower alkylated ureido, or N-cycloalkyl-substituted ureido, for example ureido, N'-lower alkylureido or N',N'-di-lower alkylureido or N'-cycloalkylureido, also lower alkylsulphonylamino; N-lower alkylated amino, such as N-lower alkylamino or N,N-di-lower alkylamino, optionally unsaturated N,N-lower alkyleneamino, N,N-aza-lower alkyleneamino, N,N-oxa-lower alkyleneamino or N,N-thia-lower alkyleneamino.

Aliphatic hydrocarbon radicals $R_1$ are especially lower alkyl, in particular lower alkyl branched at the linking carbon atom, or lower alkenyl or lower alkynyl, whereas cycloaliphatic hydrocarbon radicals are especially cycloalkyl, including polycyclic cycloalkyl, and araliphatic hydrocarbon radicals are especially phenyl-lower alkyl. Substituents of such hydrocarbon radicals are, for example, for lower alkyl: etherified hydroxy, especially phenoxy or pyridyloxy optionally substituted, for example, by functionally modified carboxy, such as by optionally N-lower alkylated carbamoyl, for example carbamoyl, N-lower alkylcarbamoyl or N,N-di-lower alkylcarbamoyl; or optionally functionally modified carboxy, such as carboxy, esterified carboxy, for example lower alkoxycarbonyl, amidated carboxy, such as optionally N-lower alkylated carbamoyl, for example carbamoyl, N-lower alkylcarbamoyl or N,N-di-lower alkylcarbamoyl, or cyano; and, for example, for the aromatic moiety of phenyl-lower alkyl-: optionally functionally modified carboxy, especially amidated carboxy, such as carbamoyl optionally substituted by lower alkyl, such as N-lower alkylcarbamoyl or N,N-di-lower alkylcarbamoyl, and/or hydroxy. Lower alkyl radicals substituted in this manner are phenoxy-lower alkyl, or preferably optionally N-alkylated carbamoyl-phenoxy-lower alkyl, pyridyloxy-lower alkyl or preferably optionally N-lower alkylated carbamoyl-pyridyloxy-lower alkyl, lower alkoxycarbonyl-lower alkyl, optionally N-lower alkylated carbamoyl-lower alkyl, or cyano-lower alkyl.

Unless specifically stated otherwise, the radicals and compounds referred to hereinbefore and hereinafter as "lower" preferably contain up to 7 carbon atoms, monovalent radicals contain especially up to 5 carbon atoms, and divalent radicals 3 to 6, especially 4 or 5, carbon atoms.

Unless specifically stated otherwise, the generic terms used hereinbefore and hereinafter preferably have the following meanings:

Lower alkyl is, for example, methyl, ethyl, n-propyl, isopropyl, n-butyl, isobutyl, sec.-butyl, tert.-butyl, n-pentyl, isopentyl, neopentyl, n-hexyl, isohexyl or n-heptyl. Lower alkyl branched at the linking carbon atom is especially isopropyl or tert.-butyl.

Lower alkenyl is especially allyl, also vinyl, 2-methallyl, but-2-enyl or 3,3-dimethallyl, whereas lower alkynyl is, for example, ethynyl or propargyl.

Lower alkoxy is, for example, methoxy, ethoxy, n-propoxy, isopropoxy, n-butoxy, isobutoxy or tert.-butoxy.

Phenyl-lower alkoxy is, for example, benzyloxy.

Lower alkylthio is, for example, methylthio, ethylthio, isopropylthio or n-butylthio.

Halogen is, for example, chlorine, bromine, fluorine or iodine.

Optionally N-lower alkylated carbamoyl is, for example, carbamoyl, N-lower alkylcarbamoyl such as N-methylcarbamoyl or N-ethylcarbamoyl, or N,N-di-lower alkylcarbamoyl such as N,N-dimethylcarbamoyl or N,N-diethylcarbamoyl.

Lower alkanoylamino is, for example, formylamino, acetylamino, propionylamino, butyrylamino or pivaloylamino.

Lower alkoxycarbonylamino is, for example, methoxycarbonylamino, ethoxycarbonylamino or tert.-butoxycarbonylamino, whereas N'-lower alkylureido and N',N'-di-lower alkylureido are, for example, N'-methylureido, N'-ethylureido, N',N'-dimethylureido or N',N'-diethylureido, whereas N'-cycloalkylureido is, for example, N'-cyclopropylureido, N'-cyclopentylureido, N'-cyclohexylureido or N'-cycloheptylureido.

Lower alkylsulphonylamino is, for example, methylsulphonylamino or ethylsulphonylamino.

Hydroxy-lower alkyl is, for example, hydroxymethyl or 1- or 2-hydroxyethyl.

Lower alkoxy-lower alkyl is, for example, lower alkoxymethyl or preferably 2-(lower alkoxy)ethyl, such as methoxymethyl, ethoxymethyl, 2-methoxyethyl, 2-ethoxyethyl or 2-isopropoxyethyl.

Lower alkylthio-lower alkyl is, for example, lower alkylthiomethyl, or especially 2-(lower alkylthio)ethyl, for example methylthiomethyl, ethylthiomethyl, 2-methylthioethyl or 2-ethylthioethyl.

Halo-lower alkyl is especially trifluoromethyl.

Optionally N-lower alkylated carbamoyl-lower alkyl is, for example, carbamoylmethyl or 1- or 2-carbamoylethyl, N-lower alkylcarbamoyl-lower alkyl, such as N-methylcarbamoylmethyl or 1- or 2-N-methylcarbamoylethyl, or N,N-di-lower alkylcarbamoyl-lower alkyl, such as N,N-dimethylcarbamoylmethyl or 1- or 2-N,N-dimethylcarbamoylethyl.

Lower alkanoylamino-lower alkyl is, for example, lower alkanoylaminomethyl or preferably 2-lower alkanoylaminoethyl, such as acetylaminomethyl, propionylaminomethyl, 2-acetylaminoethyl, 2-propionylaminoethyl, or 2-pivaloylaminoethyl, whereas lower alkoxycarbonylamino-lower alkyl is, for example, lower alkoxycarbonylaminomethyl or preferably 2-lower alkoxycarbonylaminoethyl, such as methoxycarbonylaminomethyl, ethoxycarbonylaminomethyl, 2-methoxycarbonylaminoethyl, 2-ethoxycarbonylaminoethyl or 2-tert.-butoxycarbonylaminoethyl.

Lower alkanoylamino-lower alkenyl is especially 2-lower alkanoylaminovinyl, for example 2-acetylaminovinyl, 2-propionylaminovinyl or 2-pivaloylaminovinyl, whereas lower alkoxycarbonylamino-lower alkenyl is preferably 2-lower alkoxycarbonylaminovinyl, such as 2-methoxycarbonylaminovinyl, 2-ethoxycarbonylaminovinyl or 2-tert.-butoxycarbonylaminovinyl.

Cycloalkyl, including polycyclic cycloalkyl, preferably contains 3-10 ring carbon atoms and represents cyclopropyl or especially cyclopentyl, cyclohexyl or cycloheptyl, or also adamantyl, such as 1-adamantyl.

Lower alkenyloxy is especially allyloxy, also 2-methallyloxy, vinyloxy, but-2-enyloxy or 3,3-dimethallyloxy, whereas lower alkynyloxy is, for example, propargyloxy.

Lower alkenylthio is, for example, allylthio, 2-methallylthio or but-2-enylthio.

In a lower alkoxy-lower alkoxy radical, the two oxygen atoms are preferably separated by at least 2, for example 2 or 3, carbon atoms; examples of radicals of this type are therefore methoxymethoxy or ethoxymethoxy, but especially 2-(lower alkoxy)ethoxy, for example methoxyethoxy or 2-ethoxyethoxy, and 3-(lower alkoxy)propoxy, for example 3-methoxypropoxy or 3-ethoxypropoxy.

In a lower alkylthio-lower alkoxy radical the sulphur and the oxygen atom are preferably separated from each other by at least 2, for example 2 or 3, carbon atoms; radicals of this type are therefore especially 2-(lower alkylthio)ethoxy, for example 2-methoxythioethoxy or 2-ethylthioethoxy.

Similarly, in a lower alkoxy-lower alkylthio radical the oxygen and the sulphur atom are preferably separated from each other by at least 2, for example 2 or 3, carbon atoms; radicals of this type are especially 2-(lower alkoxy)ethylthio, for example 2-methoxyethylthio or 2-ethoxyethylthio.

In lower alkanoylamino-lower alkoxy radicals and lower alkoxycarbonylamino-lower alkoxy radicals, the nitrogen atom and the linking oxygen atom are preferably separated from each other by at least 2, for example 2 or 3, carbon atoms; these radicals are especially 2-lower alkanoylaminoethoxy, for example 2-acetylaminoethoxy, 2-propionylaminoethoxy, or 2-pivaloylaminoethoxy, or 2-lower alkoxycarbonylaminoethoxy, for example 2-methoxycarbonylaminoethoxy or 2-ethoxycarbonylethoxy.

Lower alkanoyl is especially acetyl, propionyl or pivaloyl.

Lower alkanoyloxy is, for example, acetoxy, propionoxy or pivaloyloxy.

Lower alkoxycarbonyl is, for example, methoxycarbonyl, ethoxycarbonyl, or tert.-butoxycarbonyl.

N-lower alkylamino and N,N-di-lower alkylamino are for example, methylamino or ethylamino and dimethylamino or diethylamino respectively.

Optionally unsaturated N,N-lower alkyleneamino preferably contains 5-7 ring members and is especially pyrrolidino or piperidino, and also 1-pyrryl, whereas N,N-aza-lower alkyleneamino, N,N-oxa-lower alkyleneamino and N,N-thia-lower alkyleneamino preferably contain 6 ring members, in which the second ring hetero atom is separated from the linking nitrogen atom by 2 carbon atoms and in the N,N-aza-lower alkyleneamino radical is optionally substituted, for example by lower alkyl; radicals of this type are, for example, 4-methyl-1-piperidino, 4-morpholino and 4-thiomorpholino.

Phenyl-lower alkyl is, for example, benzyl or 1- or 2-phenethyl.

Pyridyloxy is, for example, pyrid-2-yloxy, pyrid-3-yloxy or pyrid-4-yloxy.

In phenoxy-lower alkyl and pyridyloxy-lower alkyl radicals $R_1$ preferably optionally containing N-lower alkylated carbamoyl as substituent, the oxygen atom and the linking carbon atom bonded to the nitrogen atom are preferably separated from each other by at least 2, for example 2 or 3, carbon atoms. Radicals of this type are especially 2-(optionally N-lower alkylated carbamoylphenoxy)lower alkyl, for example 2-(2-carbamoylphenoxy)ethyl, 2-(4-carbamoylphenoxy)ethyl, 2-(2-N-methylcarbamoylphenoxy)ethyl or 2-(4-N,N-dimethylcarbamoylphenoxy)ethyl, also 2-(optionally N-lower alkylated carbamoylpyridyloxy)lower alkyl, for example 2-(4-carbamoylpyrid-2-yloxy)ethyl, 2-(2-carbamoylpyrid-4-yloxy)ethyl or 2-(3-carbamoylpyrid-2-yloxy)ethyl.

Lower alkoxycarbonyl-lower alkyl is, for example, lower alkoxycarbonylmethyl or 1-lower alkoxycarbonylprop-2-yl, for example, methoxycarbonylmethyl, ethoxycarbonylmethyl, 1-methoxycarbonylprop-2-yl or 1-ethoxycarbonylprop-2-yl.

Optionally N-lower alkylated carbamoyl-lower alkyl is especially carbamoylmethyl, also N-lower alkylcarbamoylmethyl or N,N-di-lower alkylcarbamoylmethyl, for example N-methylcarbamoylmethyl, N-ethylcarbamoylmethyl, N,N-dimethylcarbamoylmethyl or N,N-diethylcarbamoylmethyl, also 1-carbamoylprop-2-yl, 1-N-lower alkylcarbamoylprop-2-yl or 1-N,N-di-lower alkylcarbamoylprop-2-yl, for example 1-N-methylcarbamoylprop-2-yl, 1-N-ethylcarbamoylprop-2-yl, 1-N,N-dimethylcarbamoylprop-2-yl or 1-N,N-diethylcarbamoylprop-2-yl.

Cyano-lower alkyl is, for example, cyanomethyl or 1-cyanoprop-2-yl.

In the compounds of the formula I the group $Ar_1$ preferably represents naphthyl, for example 1-naphthyl; 5,6,7,8-tetrahydronaphthyl, for example 1-(5,6,7,8-tetrahydro-6,7-dihydroxynaphthyl; fluorenyl, for example 4-fluorenyl; 9,10-ethano-9,10-dihydroanthryl, for example 9,10-dihydro-1-anthryl; indolyl, for example 4-indolyl; 2H-thiochromenyl, for example 2H-thiochromen-8-yl; lower alkylphenyl, such as methylphenyl, for example 2- or 3-methylphenyl; halo-lower alkylphenyl, such as chloromethylphenyl, for example 2-chloro-5-methylphenyl; lower alkenylphenyl, such as allylphenyl, for example 2-allylphenyl; lower alkynylphenyl, such as ethynylphenyl, for example, 2-ethynylphenyl; cycloalkylphenyl, for example 2-cyclopropylphenyl or 2-cyclopentylphenyl; hydroxyphenyl, for example 4-hydroxyphenyl; acetoxytrimethylphenyl, for example 4-acetoxy-2,3,5-trimethylphenyl; hydroxy-lower alkylphenyl, for example 2-hydroxymethylphenyl; lower alkoxy-lower alkylphenyl, such as lower alkoxymethylphenyl or (2-lower alkoxyethyl)phenyl, for example 2-methoxymethylphenyl or 4-(2-methoxyethyl)phenyl; carbamoyl-lower alkylphenyl, for example carbamoylmethylphenyl; lower alkoxycarbonylamino-lower alkylphenyl, such as (2-lower alkoxycarbonylaminoethyl)phenyl, for example 4-(2-methoxycarbonylaminoethyl)phenyl; halo-lower alkoxycarbonylamino-lower alkylpyridyl, for example 3-chloro-5-(2-methoxycarbonylamino-lower alkyl)pyridyl, such as 3-chloro-5-(2-methoxycarbonylaminoethyl)pyrid-2-yl; lower alkoxycarbonylamino-lower alkenylphenyl, especially (2-lower alkoxycarbonylaminovinyl)phenyl, for example 4-(2-methoxycarbonylaminovinyl)phenyl; lower alkoxyphenyl, such as methoxyphenyl, for example 2-methoxyphenyl; phenyl-lower alkoxyphenyl, such as benzyloxyphenyl, for example 4-benzyloxyphenyl; lower alkenyloxyphenyl, such as allyloxyphenyl, for example 2-allyloxyphenyl or methallyloxyphenyl, for example 2-(2-methallyloxy)phenyl; lower alkynyloxyphenyl, such as propargyloxyphenyl, for example 2-propargyloxyphenyl; lower alkylthio-lower alkoxyphenyl, in which the sulphur atom is separated from the oxygen atom by 2 or 3 carbon atoms, such as (2-lower alkylthioethoxy)phenyl, for example 4-(2-methylthioethoxy)phenyl; lower alkylthiophenyl, such as methylthiophenyl, for example 2-methylthiophenyl; halophenyl, such as chlorophenyl, for example 2-chlorophenyl; lower alkanoyl-lower alkanoylaminophenyl, for example 2-acetyl-4-n-butyrylaminophenyl; cyanophenyl, for example 2-cyanophenyl; lower alkanoylaminophenyl, such as acetylaminophenyl, for example 4-acetylaminophenyl; ureidophenyl, such as 4-(N'-methylureido)phenyl or 4-(N'-cycloalkylureido)phenyl, such as 4-(N'-cyclohexylureido)phenyl; lower alkylsulphonylaminophenyl, for example 4-methylsulphonylaminophenyl; (1-pyrryl)phenyl, for example 2-(1-pyrryl)phenyl; morpholinothiadiazolyl, for example 4-morpholino-1,2,5-thiadiazol-3-yl; oxo-5,6,7,8-tetrahydrobenznaphthyl, for example 5-oxo-5,6,7,8-tetrahydro-1-naphthyl, or oxo-1,2,3,4-tetrahydroquinolinyl, for example 2-oxo-1,2,3,4-tetrahydroquinolin-5-yl; pyridyl, for example pyrid-2-yl; cyanopyridyl, for example 3-cyanopyrid-2-yl; lower alkoxycarbonylamino-lower alkylpyridyl, for example 5-(ethoxycarbonylaminoethyl)pyrid-2-yl; halopyridyl, such as chloropyridyl, for example 3-chloropyrid-2-yl; lower alkoxypyridyl, such as ethoxypyridyl, for example 3-ethoxypyrid-2-yl; pyrazinyl, for example pyrazin-2-yl; lower alkylthiopyrazinyl, for example 3-ethylthiopyrazin-2-yl or pyrimidinyl, for example pyrimidin-2-yl; also optionally N-lower alkyl-substituted benzimidazolyl, such as benzimidazol-4-yl, or 1-lower alkylbenzimidazol-4-yl, such as 1-methylbenzimidazol-4-yl; 2,3-dihydro-3-oxo-4H-benz[5,6]oxazinyl, for example 2,3-dihydro-3-oxo-4H-benz[5,6]oxazin-8-yl; 4H-1,3-benzoxazin-2(1H)-onyl, for example 7-(4H-1,3-benzoxazin-2(1H)-on)yl; 2-(3H)benzoxazolonyl, for example 7-(2-(3H)-benzoxazolon)yl; 3,4-dihydro-1H-quinazolin-2-onyl, for example 5-(3,4-dihydro-1H-quinazolin-2-on)yl; tetrahydrofurfuryloxyphenyl, for example 2-tetrahydrofurfuryloxyphenyl; and $R_1$ is especially lower alkyl, especially lower alkyl branched at the linking carbon atom, for example isopropyl or tert.-butyl; also carbamoylphenoxy-lower alkyl, such as 2-carbamoylphenoxy-lower alkyl, for example 2-(4-carbamoylphenoxy)ethyl.

Compounds of the above formula I are especially the following, in which lower alkyl $R_1$ is branched at the linking carbon atom: 1-(naphthyloxy)-3-lower alkylaminopropan-2-ols, for example 3-isopropylamino-1-(1-naphthyloxy)propan-2-ol; 1-(6,7-dihydroxy-5,6,7,8-tetrahydro-1-naphthyloxy)-3-lower alkylaminopropan-2-ols, for example 3-tert.-butylamino-1-(6,7-dihydroxy-5,6,7,8-tetrahydro-1-naphthyloxy)propan-2-ol; 1-(benzfluorenyloxy)-3-lower alkylaminopropan-2-ols, for example 1-(4-fluorenyloxy)-3-isopropylaminopropan-2-ol or 3-tert.-butylamino-1-(4-fluorenyloxy)-propan-2-ol, 1-(9,10-ethano-9,10-dihydrobenz-anthryloxy)-3-lower alkylaminopropan-2-ols, for example 1-(9,10-ethano-9,10-dihydro-1-anthryloxy)-3-isopropylaminopropan-2-ol; 1-(benz-indolyloxy)-3-lower alkylaminopropan-2-ols, for example 1-(4-indolyloxy)-3-isopropylaminopropan-2-ol; 3-lower alkylamino-1-(2H-benz-thiochromenyloxy)propan-2-ols, for example 3-tert.-butylamino-1-(2H-thiochromen-8-yloxy)propan-2-ol; 3-lower alkylamino-1-(lower alkylphenoxy)propan-2-ols, in which the phenyl radical may additionally be substituted by halogen, for example 3-isopropylamino-1-(3-methylphenoxy)propan-2-ol, 1-(2-chloro-5-methylphenoxy)-3-isopropylaminopropan-2-ol or 3-tert.-butylamino-1-(2-chloro-5-methylphenoxy)propan-2-ol; 3-(carbamoylphenoxy-lower alkylamino)-1-(lower alkylphenoxy)propan-2-ols, for example 3-[2-(4-carbamoylphenoxy)-ethylamino]-1-(2-methylphenoxy)propan-2-ol; 1-(lower alkenylphenoxy)-3-lower alkylaminopropan-2-ols, for example 1-(2-allylphenoxy)-3-isopropylaminopropan-2-ol; 1-(lower alkynylphenoxy)-3-lower alkylaminopropan-2-ols, for example 1-(2-ethynylphenoxy)-3-isopropylaminopropan-2-ol; 1-(cycloalkylphenoxy)-3-lower alkylaminopropan-2-ols, for example 1-(2-cyclopropylphenoxy)-3-isopropylaminopropan-2-ol or 3-tert.-butylamino-1-(2-cyclopentylphenoxy)propan-2-ol; 1-(hydroxyphenoxy)-3-lower alkylaminopropan-2-ols, for example 1-(4-hydroxyphenoxy)-3-isopropylaminopropan-2-ol; 1-(hydroxy-lower alkylphenoxy)-3-lower alkylaminopropan-2-ols, for example 1-(2-hydroxymethylphenoxy)-3-isopropylaminopropan-2-ol; 1-acetoxytrimethylphenoxy-3-lower alkylaminopropan-2-ols, for example 1-(4-acetoxy-2,3,5-trimethylphenoxy)-3-isopropylaminopropan-2-ol; 1-(lower alkoxy-lower alkylphenoxy)-3-lower alkylaminopropan-2-ols, for example 3-isopropylamino-1-(2-methoxymethylphenoxy)propan-2-ol, 3-tert.-butylamino-1-(2-methoxymethylphenoxy)propan-2-ol or 3-isopropylamino-1-[4-(2-methoxyethyl)-phenoxy]propan-2-ol; 1-(carbamoyl-lower alkylphenoxy)-3-lower alkylaminopropan-2-ols, for example 1-(4-carbamoylmethylphenoxy)-3-isopropylaminopropan-2-ol; 1-(lower alkoxycarbonylamino-lower alkylphenoxy)-3-lower alkylaminopropan-2-ols, for example 3-isopropylamino-1-[4-(2-methoxycarbonylaminoethyl)-phenoxy]propan-2-ol; 1-(halo-lower alkoxycarbonylamino-lower alkylpyridyloxy)-3-lower alkylaminopropan-2-ols, for example 1-[3-chloro-4-(2-methoxycarbonylaminoethyl)pyrid-2-yloxy]-3-isopropylaminopropan-2-ol; 1-(lower alkoxycarbonylaminovinylphenoxy)-3-lower alkylaminopropan-2-ols, for example 3-isopropylamino-1-[4-(2-methoxycarbonylaminovinyl)phenoxy]-propan-2-ol; 1-(phenyl-lower alkoxyphenoxy)-3-lower alkylaminopropan-2-ols, for example 1-(4-benzyloxyphenoxy)-3-isopropylaminopropan-2-ol; 1-(lower alkoxyphenoxy)-3-lower alkylaminopropan-2-ols, for example 3-isopropylamino-1-(2-methoxyphenoxy)propan-2-ol; 1-(lower alkenyloxyphenoxy)-3-lower alkylaminopropan-2-ols, for example 1-(2-allyloxyphenoxy)-3-isopropylaminopropan-2-ol, 1-(2-allyloxyphenoxy)-3-tert.-butylaminopropan-2-ol or 3-isopropylamino-1-(2-methallyloxyphenoxy)propan-2-ol; 1-(lower alkynyloxyphenoxy)-3-lower alkylaminopropan-2-ols, for example 3-isopropylamino-1-(2-propargyloxyphenoxy)propan-2-ol; 3-lower alkylamino-1-(lower alkylthio-lower alkoxyphenoxy)propan-2-ols, in which the sulphur atom is separated from the oxygen atom by 2 or 3 carbon atoms, for example 3-isopropylamino-1-[4-(2-methylthioethoxy)phenoxy]propan-2-ol; 1-(halophenoxy)-3-lower alkylaminopropan-2-ols, for example 3-tert.-butylamino-1-(2-chlorophenoxy)propan-2-ol; 1-(lower alkylthiophenoxy)-3-lower alkylaminopropan-2-ols, for example 3-isopropylamino-1-(2-methylthiophenoxy)propan-2-ol; 1-(lower alkanoyl-lower alkanoylaminophenoxy)-3-lower alkylaminopropan-2-ols, for example 1-(2-acetyl-4-n-butyrylaminophenoxy)-3-isopropylaminopropan-2-ol; 1-(cyanophenoxy)-3-lower alkylaminopropan-2-ols, for example 3-tert.-butylamino-1-(2-cyanophenoxy)-propan-2-ol or 1-(2- cyanophenoxy)-3-isopropylaminopropan-2-ol; 1-(lower alkanoylaminophenoxy)-3-lower alkylaminopropan-2-ols, for example 1-(4-acetylaminophenoxy)-3-isopropylaminopropan-2-ol; 1-(N'-lower alkylureido-N-phenoxy)-3-lower alkylaminopropan-2-ols, for example 1-(N'-methylureido-N-phenoxy)-3-isopropylaminopropan-2-ol; 1-(N'-cycloalkylureidophenoxy)-3-lower alkylaminopropan-2-ols, for example 1-(N'-cyclohexylureidophenoxy)-3-tert.-butylaminopropan-2-ol; 3-lower alkylamino-1-(lower alkylsulphonylaminophenoxy)propan-2-ols, for example 3-isopropylamino-1-(4-methylsulphonylaminophenoxy)propan-2-ol; 3-lower alkylamino-1-(1-pyrryl)phenoxypropan-2-ols, for example, 3-isopropylamino-1-[2-(1-pyrryl)]phenoxypropan-2-ol; 1-(morpholinothiadiazolyloxy)-3-lower alkylaminopropan-2-ols, for example 3-isopropylamino-1-(4-morpholino-1,2,5-thiadiazol-3-yloxy)propan-2-ol; 3-lower alkylamino-1-(oxo-5,6,7,8-tetrahydrobenznaphthyloxy)propan-2-ols, for example 3-tert.-butyl-1-(5-oxo-5,6,7,8-tetrahydro-1-naphthyloxy)propan-2-ol; or 3-lower alkylamino-1-(oxo-1,2,3,4-tetrahydrobenzquinolinyloxy)propan-2-ols, for example 3-isopropylamino-1-(2-oxo-1,2,3,4-tetrahydroquinolin-5-yloxy)propan-2-ol or 3-tert.-butylamino-1-(2-oxo-1,2,3,4-tetrahydroquinolin-5-yloxy)propan-2-ol; 3-lower alkylamino-1-(pyrazin-2-yloxy)propan-2-ols, for example 3-isopropylamino-1-(pyrazin-2-yloxy)propan-2-ol; 3-lower alkylamino-1-(3-lower alkylthiopyrazin-2-yloxy)propan-2-ols, for example 3-tert.-butylamino-1-(3-ethylthiopyrazin-2-yloxy)propan-2-ol; 3-lower alkylamino-1-(pyrimidin-2-yloxy)propan-2-ols, for example 3-isopropylamino-1-(pyrimidin-2-yloxy)propan-2-ol; (3-lower alkylamino-2-hydroxypropoxy)benzimidazol-2-ones, for example 4-(3-tert.-butylamino-2-hydroxypropoxy)benzimidazol-2-one; 4-[3-[(hydroxyphenoxy)alkylamino]-2-hydroxypropoxy]benzimidazol-2-ones, for example 4-[3-[2-(4-hydroxyphenoxy)ethylamino]-2-hydroxypropoxy]benzimidazol-2-one; (3-lower alkylamino-2-hydroxypropoxy)-2,3-dihydro-(4H)-benz[5,6]oxazin-3-ones, for example 8-(3-tert.-butylamino-2-hydroxypropoxy)-2,3-dihydro-4H-benz[5,6]oxazin-3-one; (3-lower alkylamino-2-hydroxypropoxy)-3,4-dihydro-1H-quinazolin-2-ones, for example 5-(3-tert.-butylamino-2-hydroxypropoxy)-3,4-dihydro-1H-quinazolin-2-one; (3-lower alkylamino-2-hydroxypropoxy)-2(3H)-benzoxazolones, for example 7-(3-tert.-butylamino-2-hydroxypropoxy)-2(3H)-benzoxazolone; (3-lower alkylamino-2-hydroxypropoxy)-4H-1,3-benzoxazin-2(1H)-ones, for example 7-(3-tert.-butylamino-2-hydroxypropoxy)-4H-1,3-benzoxazin-2(1H)-one; 3-lower alkylamino-1-[2-(tetrahydrofurfuryloxy)-phenoxy]propan-2-ols, for example 3-tert.-butylamino-1-[2-(tetrahydrofurfuryloxy)phenoxy]propan-2-ol; 1-(cyanopyridyloxy)-3-lower alkylaminopropan-2-ols, for example 3-tert.-butylamino-1-(3-cyanopyrid-2-yloxy)prop-2-ol; 1-(halopyridyloxy)-3-lower alkylaminopropan-2-ols, for example 3-isopropylamino-1-(3-chloropyrid-2-yloxy)propan-2-ol; 1-(lower alkoxypyridyloxy)-3-lower alkylaminopropan-2-ols, for example 3-tert.-butylamino-1-(3-ethoxypyrid-2-yloxy)propan-2-ol; 1-(lower alkoxycarbonylamino-lower alkylpyridyloxy)-3-lower alkylaminopropan-2-ols, for example 3-isopropylamimo-1-[5-(2-ethoxycarbonylaminoethyl)pyrid-2-yloxy]propan-2-ol; 1-(lower alkoxycarbonylamino-lower alkylhalopyridyloxy)-3-lower alkylaminopropan-2-ols, for example 3-isopropylamino-1-[5-(2-ethoxycarbonylaminoethyl)-3-chloropyrid-2-yloxy]propan-2-ol and the salts thereof.

German Patent No. 585 164 describes a process for reversing the direction of rotation of optically active phenylalkylamines by refluxing, for example, d-m-hydroxyphenylethanolmethylamines with acetic anhydride and concentrated sulphuric acid, hydrolysing with dilute sulphuric acid the residue remaining after evaporating off the excess acetic anhydride, and isolating the l-m-hydroxyphenylethanolmethylamine from the hydrolysate.

Nagai and Kanao [Liebig's Annalen der Chemie, 470, 157–182 (1929)], in particular on page 160, state that oxazoline is produced from N-benzoyl-nor-d,l-ephedrine by means of concentrated sulphuric acid with ring closure, and this oxazoline is hydrolysed by boiling with dilute hydrochloric acid.

U.S. Pat. No. 2,446,192 describes the conversion of d,l-allothreonine into d,l-threonine in which, for example, N-acetyl- or N-benzoyl-d,l-allothreonine in the form of the methyl or ethyl ester is converted by means of thionyl chloride into the corresponding oxazoline, and this is converted by means of acid or alkaline hydrolysis into d,l-threonine. In addition to thionyl chloride, phosphorus pentachloride, phosphorus trichloride and phosphorus pentoxide are mentioned as other possible dehydration and cyclisation agents, but thionyl chloride is preferred.

From J. Amer. Chem. Soc., 70, 2297–98 (1948), it is furthermore known to convert N-benzoyl-d,l-allothreonine methyl ester into the corresponding oxazoline hydrochloride by means of thionyl chloride and, from this, d,l-threonine is obtained by hydrolysis with dilute hydrochloric acid. Following this it is stated that the described oxazoline inversion is a generally applicable method for the reciprocal conversion of diastereoisomeric α,β-amino-alcohols in high yields. In the described processes, in each case secondary N-acylaminoalcohols are used as starting material, the hydrogen atom disposed at the nitrogen atom being eliminated during the formation of the oxazoline ring.

According to Chemical Abstracts 84, 43593x (1976), derivatives of phenyl- and phenoxy-ethanolamine are reacted with haloformic acid esters and the resulting N-alkoxycarbonyl compounds are cyclised by means of thionyl chloride or bromide to form the corresponding oxazolidinones. From these, the compounds corresponding to the starting materials with an inverted steric configuration are obtained by means of alkaline hydrolysis or reduction with lithium aluminium hydride.

H. K. Müller Ann. 599, 211–221 (1956) states, with reference to the above-mentioned literature source, viz. W. N. Nagai and S. Kanao, that the rearrangement of N-benzoyl-d,l-norephedrine is effected with more favourable yields if thionyl chloride is used instead of sulphuric acid, and that owing to the fact that the resulting intermediate is more readily hydrolysable, N-acetyl-d,l-norephedrine is even more suitable as a starting material for d,l-pseudoephedrine. Starting from the N-acetyl derivative an unstable preliminary product to the corresponding oxazoline, viz 2-chloro-2,4-dimethyl-5-phenyloxazolidine hydrochloride, is also isolated, and furthermore the structure of the oxazoline is confirmed by producing the isomeric d,l-threo-1-phenyl-1-chloro-2-acetamidopropane hydrochloride with distinctly different properties by reacting d,l-norephedrine with thionyl chloride followed by N-acetylation.

An advantageous process for the configuration inversion of α-amino-alcohols with a primary amino group is to be found in the state of the art especially in the process comprising N-acylation, especially N-acetylation, conversion of the N-acyl derivatives into the corresponding oxazolines by means of thionyl chloride and hydrolysis, preferably alkaline hydrolysis, and there are also other suitable processes available.

On the other hand, configuration inversion of α-amino-alcohols with a secondary amino group has hitherto been effected only by N-acylation, boiling the N-acyl derivative with concentrated sulphuric acid in acetic anhydride and hydrolysing the reaction product of unknown constitution with dilute sulphuric acid. When this process was used for d-pseudeophedrine, a yield of only 65% of the inversion product was obtained, which in the case of a monostereoisomeric compound would correspond to a yield of only approximately 30% of inversion product together with approximately 70% of racemate which would have to be resolved again. In addition, and more especially, the conversion of N-acyl compound into oxazoline requires rather vigorous reaction conditions. On the other hand, it is known, for example, from Chemical Reviews 54, 614–685, especially 632 and 633, (1954) and the literature quoted therein, that many aralkyl ethers are split into glacial acetic acid if boiled with sulphuric acid. It has also been found that the analogous application of the afore-mentioned process described by Nagai and Kanao to configuration inversion, for example in S(—)-1-(4-benzyloxyphenoxy)-3-isopropylaminopropan-2-ol for the purpose of producing the corresponding R(+) compound, results merely in a product that is extremely contaminated, essentially because of the ether splitting. Such a result inevitably leads to the conclusion that the known process applied to ether derivatives of 3-alkylaminopropan-2-ol would lead only to unsatisfactory results.

In view of this it could not be expected that a similar configuration inversion could be carried out in optically active compounds of the 1-aryloxy-3-secondary aminopropan-2-ol type. The reaction sequence that can be effected with great success with α-primary amino-alcohols under relatively mild reaction conditions, that is of reacting an N-acyl derivative, for example, the N-acetyl compound, for example with thionyl chloride, to form an oxazoline compound as middle process step, was never even considered for use with 1-aryloxy-3-secondary aminopropan-2-ols because the formation of an oxazoline did not seem possible owing to the absence of a hydrogen atom at the nitrogen atom of an N-acylated starting material.

Surprisingly it has now been found that an inversion of the configuration in optically active compounds of the formula I can be effected by converting an optically active compound of the formula

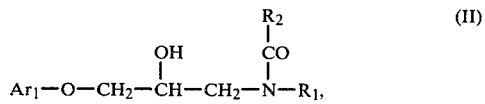

having an

R(+) or S(—) configuration, in which

R$_2$ represents a monocyclic or polycyclic, carbocyclic or heterocyclic radical, or an optionally substituted aliphatic, cycloaliphatic or aralphatic hydrocarbon radical, by treating with a strong, oxygen-containing inorganic or organic acid or halides thereof, into an optically active compound of the formula

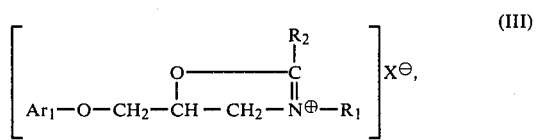

in which

X$^\ominus$ represents the anion of a strong, oxygen-containing inorganic or organic acid or of a halogen atom, and hydrolysing the resulting compound of the formula III, optionally by way of the corresponding free base as intermediate, to form a compound of the formula I with a configuration opposite to that of the starting material used and, if desired, converting a free compound of the formula I into a salt, or a resulting salt into the free compound.

Suitable strong, oxygen-containing inorganic or organic acids are for example, concentrated sulphuric acid or phosphoric acid or a strong organic sulphonic acid, such as an aliphatic sulphonic acid, for example methanesulphonic acid, or an aromatic sulphonic acid, such as an optionally substituted phenylsulphonic acid, for example 4-methyl-, 4-bromo-, 4-nitro- or 2,4-dinitrophenylsulphonic acid, or a naphthylsulphonic acid, for example 1-naphthylsulphonic acid, or halides thereof, especially chlorides or bromides, such as thionyl chloride, thionyl bromide, sulphuryl chloride, chlorosulphonic acid, phosphorus trichloride, phosphorus pentachloride, phosphorus oxychloride or methanesulphonyl chloride. It is also possible to use mixed esters corresponding to the mentioned halides, such as a lower alkoxysulphonyl halide, for example methoxysulphonyl or ethoxysulphonyl chloride, or phosphoric acid lower alkyl ester halides, for example phosphoric acid dimethyl ester chloride.

Accordingly, in the formula III X$^\ominus$ represents the anion especially of chlorine or bromine, of sulphuric acid, of phosphoric acid or of a strong organic sulphonic acid, for example one of those mentioned.

If one of the mentioned acids is used as condensing agent, the cyclising condensation is usually carried out in a temperature range of from approximately 50° to 200° and, if a halide is used, in a temperature range of from −10° to 70°, preferably 10° to 50°.

The hydrolysis is carried out in an acid or basic medium. Suitable acidic agents are, for example, aqueous acids, for example aqueous mineral acids, such as aqueous hydrochloric acid, sulphuric acid or phosphoric acid. The acid hydrolysis is carried out in a temperature range of from 0° to 120°, advantageously 10° to 50°. Suitable basic media are, for example, aqueous alkaline solutions such as those of alkali metals or alkaline earth metals, such as sodium hydroxide, or potassium hydroxide, or the hydroxides of calcium or magnesium, the said reagents advantageously being used at elevated temperature, for example in a range of from 50° to 150°.

The hydrolysis can alternatively be carried out in stages by hydrolysing in aqueous medium a compound of the formula III, optionally by way of the corresponding free base as intermediate, to form the corresponding N-acyl compound of the formula II having an inverted steric configuration like that of the particular starting material of the formula II used, and subsequently hydrolysing this compound to form a compound corresponding to the formula I.

The process according to the invention may advantageously be carried out in the manner that a starting material of the formula II used in situ, without being isolated in pure form, is further processed in the same reaction mixture to form the compound of the formula III and this compound is then subjected to hydrolysis without further purification.

In a starting material of the formula II or an intermediate of the formula III $R_2$ has, for example, a meaning corresponding to the radical $Ar_1$ or to the radical $R_1$, and represents especially optionally substituted, for example as stated, phenyl, naphthyl or pyridyl, or also lower alkyl such as isopropyl or tert.-butyl, or phenyl-lower alkyl or phenoxy-lower alkyl with lower alkyl optionally branched at the linking carbon atom, for example 1-methyl-3-phenylpropyl or 1-methyl-3-phenoxypropyl.

The invention relates furthermore to a particular embodiment of the process according to the invention in which an optically active starting material of the formula II, in which $Ar_1$ represents naphthyl, lower alkylphenyl, lower alkenylphenyl, lower alkenyloxyphenyl, lower alkanoylaminophenyl, lower alkoxy-lower alkylphenyl, 9,10-ethano-9,10-dihydrobenzanthryl, pyrazinyl, pyrimidinyl, indolyl, benzofuryl, cyanopyridyl, pyrrylphenyl, lower alkoxycarbonylamino-lower alkylpyridyl, N'-cycloalkylureidophenyl, (benzimidazol-2-on)yl, phenyl-lower alkoxyphenyl or hydroxyphenyl, $R_1$ represents lower alkyl, phenyl-lower alkyl, phenoxy-lower alkyl or pyridyloxy, and $R_2$ represents lower alkyl, phenyl-lower alkyl or phenyl, is reacted with concentrated phosphoric acid or concentrated sulphuric acid or a halide of such acids, and the resulting compound of the formula III is hydrolysed, optionally by way of the corresponding free base as intermediate, to form the corresponding compound of the formula I having an opposite configuration.

The invention further relates to a particular embodiment of the process according to the invention in which an optically active starting material of the formula II in which $Ar_1$ represents 1-naphthyl, 3-lower alkylphenyl, 2-lower alkenylphenyl, 2-lower alkenyloxyphenyl, 4-lower alkanoylaminophenyl, 4-(2-lower alkoxyethyl)phenyl, pyrazin-2-yl, pyrimidin-2-yl, (1-pyrryl)-phenyl, 4-indolyl, 5-(2-lower alkoxycarbonylaminoethyl)pyridyl, 3-cyanopyridyl, 4-(benzimidazol-2-on)yl, 4-(N'-cycloalkylureido)phenyl, benzyloxyphenyl or hydroxyphenyl, and $R_1$ represents lower alkyl, phenyl-lower alkyl or phenoxy-lower alkyl, and $R_2$ represents lower alkyl phenyl-lower alkyl or phenyl, is reacted with concentrated phosphoric acid or concentrated sulphuric acid or a chloride or bromide of such acids and the resulting compound of the formula III is hydrolysed, optionally by way of the corresponding free base as intermediate, to form the corresponding compound of the formula I having an opposite configuration.

The invention further relates to a particular embodiment of the process according to the invention in which an optically active starting material of the formula II in which $Ar_1$ represents 1-naphthyl, 3-methylphenyl, 2-allylphenyl, 2-allyloxyphenyl, 4-acetylaminophenyl, 4-indolyl, 4-(2-methoxyethyl)phenyl, pyrazin-2-yl, pyrimidin-2-yl, 2-(1-pyrryl)phenyl, 4-(N'-cyclohexylureido)phenyl, 4-benzyloxyphenyl or 4-hydroxyphenyl, $R_1$ represents lower alkyl or phenyl-lower alkyl, and $R_2$ represents lower alkyl, phenyl-lower alkyl or phenyl, is reacted with concentrated phosphoric acid or concentrated sulphuric acid or a chloride or bromide of such acids and the resulting compound of the formula III is hydrolysed, optionally by way of the corresponding free base as intermediate, by means of aqueous mineral acid or aqueous alkali metal hydroxide solution to form the corresponding compound of the formula I having an opposite configuration.

The invention furthermore relates to a particular embodiment of the process in which an optically active starting material of the formula II in which $Ar_1$ represents 2-(1-pyrryl)phenyl, 1-naphthyl, 2-allylphenyl, 2-allyloxyphenyl, 4-(N'-cyclohexylureido)phenyl, pyrazin-2-yl, 4-benzyloxyphenyl or 4-hydroxyphenyl, $R_1$ represents lower alkyl, and $R_2$ represents lower alkyl or phenyl, is reacted with concentrated sulphuric acid or a chloride thereof, or with thionyl chloride, and the resulting compound of the formula III is hydrolysed, optionally by way of the corresponding free base as intermediate, by means of aqueous hydrochloric or sulphuric acid or aqueous alkali metal hydroxide solution to form the corresponding compound of the formula I having an opposite configuration.

The invention relates especially to the processes described in the Examples.

The invention relates furthermore to optically active compounds of the formula III in which $Ar_1$, $R_1$, $R_2$ and X have the meanings given above, or to such compounds in the form of free bases.

The invention also relates to optically active compounds of the formula III in which X represents a halogen atom or the radical of sulphuric or phosphoric acid, $Ar_1$ represents naphthyl, lower alkylphenyl, lower alkenylphenyl, lower alkenyloxyphenyl, lower alkanoylaminophenyl, lower alkoxy-lower alkylphenyl, 9,10-ethano-9,10-dihydrobenz-anthryl, pyrazinyl, pyrimidinyl, indolyl, benzofuryl, cyanopyridyl, pyrrylphenyl, lower alkoxycarbonylamino-lower alkylpyridyl, N'-cycloalkylureidophenyl, (benzimidazol-2-on)yl, phenyl-lower alkoxyphenyl or hydroxyphenyl, $R_1$ represents lower alkyl, phenyl-lower alkyl, phenoxy-lower alkyl or pyridyloxy, and $R_2$ represents lower alkyl, phenyl-lower alkyl, phenoxy-lower alkyl or phenyl, or such compounds in the form of free bases.

The invention relates furthermore to optically active compounds of the formula III in which X represents chlorine or bromine or the radical of sulphuric or phosphoric acid, $Ar_1$ represents 1-naphthyl, 3-lower alkylphenyl, 2-lower alkenylphenyl, 2-lower alkenyloxyphenyl, 4-lower alkanoylaminophenyl, 4-(2-lower alkoxyethyl)-phenyl, pyrazin-2-yl, pyrimidin-2-yl, (1-pyrryl)phenyl, 4-indolyl, 5-(2-lower alkoxycarbonylaminoethyl)pyridyl, 3-cyanopyridyl, 4-(benzimidazol-2-on)yl, 4-(N'-cycloalkylureido)phenyl, benzyloxyphenyl or hydroxyphenyl, $R_1$ represents lower alkyl, phenyl-lower alkyl or phenoxy-lower alkyl, and $R_2$ represents lower alkyl, phenyl-lower alkyl or phenyl, or such compounds in the form of free bases.

The invention also relates to optically active compounds of the formula III, in which X represents chlorine or bromine or the radical of sulphuric or phosphoric acid, $Ar_1$ represents 1-naphthyl, 3-methylphenyl, 2-allylphenyl, 2-allyloxyphenyl, 4-acetylaminophenyl, 4-indolyl, 4-(2-methoxyethyl)phenyl, pyrazin-2-yl, pyrimidin-2-yl, 2-(1-pyrryl)phenyl, 4-(N'-cyclohexylureido)phenyl, 4-benzyloxyphenyl or 4-hydroxyphenyl, $R_1$ represents lower alkyl or phenyl-lower alkyl and $R_2$ represents lower alkyl, phenyl-lower alkyl or phenyl, or such compounds in the form of free bases.

The invention also relates to optically active compounds of the formula III in which X represents chlorine or the radical of sulphuric acid, $Ar_1$ represents 2-(1-pyrryl)phenyl, 1-naphthyl, 2-allylphenyl, 2-allyloxyphenyl, 4-(N'-cyclohexylureido)phenyl, pyrazin-2-yl, 4-benzyloxyphenol or 4-hydroxyphenyl, $R_1$ represents alkyl and $R_2$ represents lower alkyl or phenyl, or such compounds in the form of free bases.

The invention relates particularly to the compounds of formula III described in the Examples.

Depending on the conditions of the process and the starting materials, optically active compounds of the formula I are obtained in free form or in the form of their salts, which is also covered by the invention, wherein the new compounds or salts thereof may alternatively be present in the form of hemihydrates, monohydrates, sesquihydrates or polyhydrates. Acid addition salts of the new compounds can be converted into the free compounds in a manner known per se, for example by treating with basic agents, such as alkali metal hydroxides, carbonates or bicarbonates or ion exchangers. On the other hand, resulting free bases may form acid addition salts with organic or inorganic acids, for example with the acids mentioned and to produce these acid addition salts the acids used are especially those that are suitable for the formation of pharmaceutically acceptable salts.

These or other salts, especially acid addition salts of the new compounds, such as, for example, picrates or perchlorates, may also be used to purify the resulting free bases by converting the free bases into the salts, separating and purifying them, and liberating the bases from the salts again.

Salts of optically active compounds of the formula I are acid addition salts, and especially pharmaceutically acceptable, non-toxic acid addition salts with suitable inorganic acids, such as hydrochloric acid, hydrobromic acid, sulphuric acid or phosphoric acid, or with suitable organic, such as aliphatic, cycloaliphatic, aromatic, araliphatic or heterocyclic, carboxylic or sulphonic acids, such as formic acid, acetic acid, propionic acid, succinic acid, glycolic acid, lactic acid, malic acid, tartaric acid, citric acid, ascorbic acid, maleic acid, fumaric acid, pyroracemic acid, benzoic acid, anthranilic acid, 4-hydroxybenzoic acid, salicylic acid, phenylacetic acid, embonic acid, methanesulphonic acid, ethanesulphonic acid, hydroxyethanesulphonic acid, ethylenesulphonic acid, 4-chlorobenzenesulphonic acid, toluenesulphonic acid, naphthalenesulphonic acid, sulphanilic acid or cyclohexylaminesulphonic acid. As a result of the close relationship between the new compounds in free form and in the form of their salts, "free compounds" is to be understood as covering also the corresponding salts and vice versa.

The invention relates also to those embodiments of the process in which a compound obtainable as intermediate at any stage of the process is used as starting material and the remaining process steps are carried out, in which the process is interrupted at any stage, in which a starting material is formed under the reaction conditions, or in which a reactant is optionally present in the form of its salts.

Advantageously the starting materials used for carrying out the reactions according to the invention are those that result in the specifically mentioned classes of end products mentioned at the beginning and especially in the specifically described or emphasised end products.

The starting materials are known or, if they are new, can be obtained according to methods that are known per se, for example, analogously to those methods described in the Examples. For example, a compound of the formula I can be reacted in a manner known per se with a carboxylic acid of the formula $R_2$—COOH (IIa) in which $R_2$ has the meaning given, or with a reactive derivative thereof, for example a suitable reactive ester, for example a lower alkyl ester such as methyl ester, or an aromatic ester such as phenyl, 4-nitrophenyl, or 2,4-dinitrophenyl ester, or with a halide, such as a chloride or bromide, or an anhydride, such as a symmetric or mixed anhydride, to form the corresponding acylated compound of the formula II.

New starting materials of the formulae I and II and new end products also form part of the invention. The invention also relates to intermediates of the formula III obtainable in accordance with the process.

The following Examples illustrate the invention; temperatures are quoted in degrees Centigrade.

EXAMPLE 1

18 g of acetic anhydride are added dropwise at 10° to a solution of 26.2 g of R(+)-1-(4-benzyloxyphenoxy)-3-isopropylamino-propan-2-ol in 78 ml of dimethylformamide. The solution is stirred for 2 hours at 2°, then poured into 300 ml of water and extracted with 160 ml of toluene. The toluene solution is washed with sodium bicarbonate solution, dried over sodium sulphate and concentrated by evaporation in vacuo. Crude R(+)-1-(4-benzoyloxyphenoxy)-3-N-isopropyl-N-acetylamino-propan-2-ol is obtained.

This is dissolved in 40 ml of methylene chloride and added dropwise at 5°-10°, over a period of 45 minutes, to a solution of 6.2 ml of thionyl chloride in 18 ml of methylene chloride. The solution is stirred for 2 hours at 20°, then for 1 hour at 35°, and subsequently evaporated to dryness in vacuo.

32 g (93%) of crude S(−)-1-isopropyl-2-methyl-5-(4-benzyloxyphenoxymethyl)oxazolinium chloride are obtained in the form of a thick oil which soon crystallises. The hygroscopic crystals contain 1 mole of crystal hydrogen chloride. After recrystallisation from a mixture of methylene chloride and ethyl acetate the compound melts at 78°–82°.

25 ml of water, 100 ml of ethanol and 16 g of sodium hydroxide are added to the 32 g of the crude S(−)-1-isopropyl-2-methyl-5-(4-benzyloxyphenoxymethyl)oxazolinium chloride and the mixture is refluxed for 1 hour, after which it is poured into 300 ml of water and cooled to 0°. The precipitated crystals are suction-filtered and dried; 23.6 g (90% of the theoretical yield) of S(−)-1-(4-benzyloxyphenoxy)-3-isopropylaminopropan-2-ol are obtained.

| $[\alpha]_D^{20}$ | starting material: | ≈25° | (1% solution in 1N sulphuric acid) |
|---|---|---|---|
| $[\alpha]_D^{20}$ | end product: | ≈−22° | (1% solution in 1N sulphuric acid) |
| | Optical yield: | 87% | |

R(+)-1-(4-benzyloxyphenoxy)-3-isopropylaminopropan-2-ol can be obtained, for example, as follows:

(a) 4.5 g of (+)-1-(4-hydroxyphenoxy)-2-hydroxy-3-(isopropylamino)propane are dissolved in 30 ml of methanol and a solution of 8.1 g of (−)-di-O,O′-p-toluoyl-L-tartaric acid in 25 ml of methanol and 25 ml of water is added. The solution is then concentrated at room temperature in a water jet vacuum until slight turbidity occurs and it is then left at 0° for 15 hours to crystallise. The precipitated crystals are suction-filtered and then recrystallised twice from a mixture of methanol and water (1:1) R(+)-1-(4-hydroxyphenoxy)-2-hydroxy-3-isopropylaminopropan-(−)-di-O,O′-p-toluoyl-L-hydrogen tartrate is obtained;
melting point: 134°–137°.

To isolate the free enantiomeric base, the salt is taken up in 2 N hydrochloric acid and extracted by shaking with ethyl acetate. (−)-di-O,O′-p-toluoyl-D-tartaric acid can be regenerated from this extract. The hydrochloric acid solution is made alkaline with concentrated ammonia, saturated with sodium chloride and extracted by shaking with ethyl acetate. The organic phase is washed with brine, dried over sodium sulphate and concentrated by evaporation in a water jet vacuum. The residue crystallises from ethyl acetate, resulting in pure R(+)-1-(4-hydroxyphenoxy)-3-isopropylaminopropan-2-ol;
melting point: 129°–130°.

| $[\alpha]_D^{20}$: | 0.9 ± 0.5° | (1% solution in methanol). |
|---|---|---|
| $[\alpha]_D^{20}$: | 20.5 ± 0.5° | (1% solution in 1N sulphuric acid). |

(b) 42 g of a 50% solution of sodium hydroxide in water are added at room temperature to a solution of 52 g of R(+)-1-(4-hydroxyphenoxy)-3-isopropylaminopropan-2-ol hydrochloride in dimethylformamide. 33 g of benzyl bromide are added dropwise to this mixture at 30° over a period of 15 minutes and the mixture is stirred for 1 hour at room temperature. The reaction mixture is introduced into 600 ml of water cooled to 0° and stirred for one hour at 0°; the precipitated crystals are suction-filtered and dried, resulting in R(+)-1-(4-benzyloxyphenoxy)-3-isopropylaminopropan-2-ol having a melting point of 91°–93°.

EXAMPLE 2

6.5 g of S(−)-1-(4-hydroxyphenoxy)-3-isopropylaminopropan-2-ol are introduced in portions into 25 ml of acetic anhydride while stirring resulting, with the evolution of heat, in a clear solution. A solution of 3 g of sulphuric acid (96% strength) in 10 ml of acetic anhydride is added to this solution and the mixture is refluxed for 2 hours. The resulting solution is then concentrated in vacuo. The residue is crude R(+)-1-isopropyl-2-methyl-5-(4-hydroxyphenoxymethyl)oxazolinium sulphate and this is taken up in 50 ml of 1 N sulphuric acid and refluxed for 2 hours. 100 g of ice are then added and the pH is adjusted to 9 with ammonia. The solution is extracted 4 times with 100 ml of ethyl acetate each time and the combined organic phases are dried over sodium sulphate and evaporated to dryness. 5.5 g (85% of the theoretical yield) of R(+)-1-(4-hydroxyphenoxy)-3-isopropylaminopropan-2-ol are obtained.

| $[\alpha]_D^{20}$: | starting material: | −20.5° | (1% solution in 1N sulphuric acid) |
|---|---|---|---|
| $[\alpha]_D^{20}$: | end product: | 17.3° | (1% solution in 1N sulphuric acid) |
| | Optical yield: | 85%. | |

EXAMPLE 3

6.5 g of S(−)-1-(4-benzyloxyphenoxy)-3-isopropylaminopropan-2-ol are introduced in portions into 25 ml of acetic anhydride while stirring, resulting, with the evolution of heat, in a clear solution. A solution of 3 g of sulphuric acid (96%) in 10 ml of acetic anhydride is added, and the mixture is refluxed for 2 hours. Subsequently the resulting solution is concentrated in vacuo and the residue is taken up in 50 ml of 1 N sulphuric acid and refluxed for 2 hours. 100 g of ice are then added, and the pH is adjusted to 9 with ammonia. The solution is extracted 4 times with 100 ml of ethyl acetate each time; the combined organic phases are dried over sodium sulphate and then evaporated to dryness. 3.5 g of a residue consisting of strongly contaminated R(+)-1-(4-hydroxyphenoxy)-3-isopropylaminopropan-2-ol are obtained.

EXAMPLE 4

0.9 g of D(+)-1-(o-allyloxyphenoxy)-3-isopropylaminopropan-2-ol is dissolved in 5 ml of dimethylformamide and 0.34 ml of acetic anhydride is added dropwise at 10°. The solution is stirred for 2 hours at 20°, poured into 25 ml of water and extracted twice with 30 ml of toluene each time. The toluene solution is dried over magnesium sulphate then concentrated to dryness in vacuo; crude D(+)-1-(o-allyloxyphenoxy)3-N-isopropyl-N-acetylaminopropan-2-ol is obtained. This is dissolved in 5 ml of methylene chloride and added dropwise at 5°–10° over the course of 45 minutes to a solution of 0.6 ml of thionyl chloride in 5 ml of methylene chloride. The mixture is then stirred for 2 hours at 20°, then for 1 hour at 35°, then evaporated to dryness in vacuo. The residue is crude L(−)-1-isopropyl-2-methyl-5-(o-allyloxyphenoxymethyl)oxazolinium chloride. 1.0 g of sodium hydroxide is added to a solution of this compound in a mixture of 1 ml of water and 10 ml of ethanol, and the mixture is refluxed for 1 hour then poured into 25 ml of water. The solution is extracted twice with 25 ml of toluene each time and the combined organic phases are dried over magnesium sulphate then evaporated to dryness in vacuo. The residue is dissolved in 2.5 ml of cyclohexanol and the solution is cooled; the precipitated crystals are suction-filtered, and 0.7 g (78% of the theoretical yield) of L(−)-1-(o-allyloxyphenoxy)-3-isopropylaminopropan-2-ol is obtained.

| $[\alpha]_D$ | starting material: | 13.5 ± 0.5° | (1% solution in 1N sulphuric acid) |
|---|---|---|---|
| $[\alpha]_D$ | end product: | −12.7 ± 0.5 | (1% solution in 1N sulphuric acid) |
| | Optical yield: | 94% | |

The D(+)-1-(o-allyloxyphenoxy)-3-isopropylaminopropan-2-ol used as starting material can be produced as follows:

265 g (1 mole) of racemic 1-(o-allyloxyphenoxy)-3-isopropylaminopropan-2-ol and 140 g (0.95 mole) of L(+)-glutamic acid ($[\alpha]_{546}^{20} = 36° \pm 2°$, 5% solution in 5 N aqueous hydrochloric acid) are thoroughly mixed in a mortar and the mixture is dissolved in 470 ml of water heated to 70°. The warm solution is filtered clear, 2300 ml of 96% ethanol are added to the colourless filtrate and the solution is left to stand for 24 hours at 50°. The resulting crystalline precipitate is suction filtered, washed with 200 ml of ethanol and dried in air. 220 g of crude D(+)-1-(o-allyloxyphenoxy)-3-isopropylaminopropan-2-ol.L(+)-glutamate having a melting point of 172°-173° are obtained. This is dissolved in 100 ml of water at 70° and 800 ml of methanol are added to the solution. After standing for 15 hours at 5°, the resulting precipitate is suction-filtered, yielding 210 g of the enantiomeric salt having a melting point of 176°-178°. Further recrystallisation under the same conditions yields 125 g of pure D(+)-1-(o-allyloxyphenoxy)-3-isopropylaminopropan-2-ol.L(+)-glutamate, which after drying for 8 hours at 60°/0.03 mm Hg has the following characteristics:

| melting point: | 179–181° | |
|---|---|---|
| $[\alpha]_{313}$: | 34 ± 1° | (1% solution in water) |
| $[\alpha]_D$: | 7.2° | (1% solution in water) |

Elementary analysis calculated for $C_{15}H_{23}NO_3 \cdot C_5H_9NO_4$:

| C | (calculated in %): | 58.2 | H | (calculated): | 7.8 |
|---|---|---|---|---|---|
| | (found): | 58.2 | | (found): | 7.9 |
| N | (calculated): | 6.8 | | | |
| | (found): | 6.7 | | | |

By adding aqueous ammonia to the aqueous solution of D(+)-1-(o-allyloxyphenoxy)-3-isopropylaminopropan-2-ol.L(+)-glutamate until alkaline reaction occurs, then extracting with methylene chloride, evaporating to dryness and recrystallising the residue from ether and hexane, the free base having a melting point of 55°-56° is obtained. The hydrochloride has the following properties:

| melting point: | 72–74° | |
|---|---|---|
| $[\alpha]_D^{20}$: | 19 ± 1° | (1% solution in ethanol). |

By adding aqueous ammonia to the combined mother liquors until alkaline reaction occurs, then extracting with methylene chloride and evaporating off the same, a product is obtained in which the L(−)-antipode is present in concentrated form. From this product it is possible by the analogous application of the process described, using D(−)-glutamic acid, to obtain the corresponding L(−)-1-(o-allyloxyphenoxy)-3-isopropylaminopropan-2-ol, the hydrochloride of which has the following properties:

| melting point: | 73–75° | |
|---|---|---|
| $[\alpha]_D^{20}$: | −19 ± 1° | (1% solution in ethanol). |

EXAMPLE 5

0.9 g of (−)-1-(1-naphthyloxy)-3-isopropylaminopropan-2-ol hydrochloride is dissolved in 10 ml of water, 4 ml of 1 N sodium hydroxide solution are added, and the mixture is extracted three times with 25 ml of ethyl acetate each time. The organic solution is dried over magnesium sulphate and concentrated by evaporation in vacuo. The free base obtained as residue is dissolved in 5 ml of dimethylformamide and 0.34 ml of acetic anhydride is added dropwise to this solution at 10°. This solution is stirred for 2 hours at 20°, poured into 25 ml of water and extracted twice with 30 ml of toluene each time. After drying over magnesium sulphate the toluene solution is evaporated to dryness in vacuo, yielding crude (−)-1-(1-naphthyloxy)-3-N-isopropyl-N-acetylaminopropan-2-ol. This is dissolved in 5 ml of methylene chloride and added dropwise at 5°-10° over a period of 45 minutes to a solution of 0.6 ml of thionyl chloride in 5 ml of methylene chloride. The mixture is then stirred for 2 hours at 20° and for one hour at 35° and subsequently evaporated to dryness in vacuo. The oily residue is crude (+)-1-isopropyl-2-methyl-5-[1-naphthyloxymethyl]oxazolinium chloride. 1 g of sodium hydroxide is added to a solution of this compound in 1 ml of water and 10 ml of ethanol and the mixture is refluxed for 1 hour. The reaction mixture is then poured into 25 ml of water, extracted twice with 25 ml of toluene each time and the toluene layers are dried over magnesium sulphate then evaporated to dryness in vacuo.

The residue is dissolved in 5 ml of isopropanol and neutralised against methyl red with a solution of hydrochloric acid gas in isopropanol. The precipitated crystals are suction-filtered and 0.7 g (78% of the theoretical yield) of (+)-1-(1-napthyloxy)-3-isopropylaminopropan-2-ol hydrochloride is obtained.

| $[\alpha]_D$ | starting material: | −13.2 ± 0.5° | (1% solution in water, 20°) |
|---|---|---|---|
| $[\alpha]_D$ | end product: | 13.7 ± 0.5° | (1% solution in water, 20°) |
| | Optical yield: | 100%. | |

The (−)-1-(1-naphthyloxy)-3-isopropylaminopropan-2-ol-1-hydrochloride used as starting material can be obtained analogously to the process of racemate division described in Example 4. These starting materials have the following properties:

(+)-1-(1-naphthyloxy)-3-isopropylaminopropan-2-ol hydrochloride:

| melting point: | 192–193° | |
|---|---|---|
| $[\alpha]_D^{20}$: | 25 ± 1° | (1% solution in ethanol); |

(−)-1-(1-naphthyloxy)-3-isopropylaminopropan-2-ol hydrochloride:

| melting point: | 192–193° |
| --- | --- |
| $[\alpha]_D^{20}$: | −25 ± 1° (1% solution in ethanol). |

I claim:

1. A process for inverting the configuration in an optically active compound of the formula

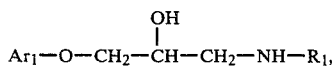

in which

Ar₁ represents 1-naphthyl, 3-lower alkylphenyl, 2-lower alkenylphenyl, 2-lower alkenyloxyphenyl, 4-lower alkanoylaminophenyl, 4-(2-lower alkoxy ethyl)-phenyl, pyrazin-2-yl, pyrimidin-2-yl, (1-pyrryl)-phenyl, 4-indolyl, 5-(2-lower alkoxy carbonylamino ethyl)pyridyl, 3-cyanopyridyl, 4-(benzimidazol-2-on)-yl, 4-(N'-cycloalkylureido)-phenyl, benzyloxyphenyl or hydroxyphenyl, R₁ represents lower alkyl, phenyl-lower alkyl or phenoxy-lower alkyl, said compound of the formula I or R(+) configuration being converted into one of S(−) configuration, or said compound of the formula I of S(−) configuration being converted into one of R(+) configuration, said configuration inversion being concerned with the secondary alcohol group being present in the group

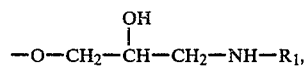

which comprises converting an optically active compound of the formula

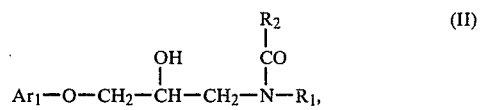

having a R(+) or S(−) configuration, in which R₂ represents lower alkyl, phenyl-lower alkyl, phenoxy-lower alkyl or phenyl, and Ar₁ and R₁ have the meaning given, by treating with concentrated phosphoric acid or concentrated sulphuric acid for two hours in a temperature range of from approximately 50° to 200°, or with a chloride or bromide of such acids for 45 minutes in a temperature range of from −10° to 70° into an optically active compound of the formula

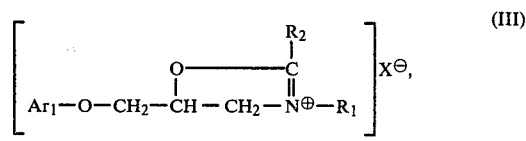

wherein $X^{\ominus}$ represents the anion of phosphoric acid or sulphuric acid or of chlorine or bromine, and hydrolysing a resulting compound of the formula III, optionally by way of the corresponding free base as intermediate, with aqueous mineral acids for 1–2 hours in a temperature range of from 0° to 120°, or with aqueous alkaline solutions for one hour in a temperature range of from 50° to 150° to form a compound of the formula I of a configuration opposite to that of the starting material used and, if desired, converting an acid addition salt of a compound of the formula I with mineral acids into the free compound, or converting a free compound of the formula I into a pharmaceutically acceptable, non-toxic acid addition salt with inorganic acids or with organic acids.

* * * * *

UNITED STATES PATENT AND TRADEMARK OFFICE
CERTIFICATE OF CORRECTION

PATENT NO. : 4,294,966

DATED : OCTOBER 13, 1981

INVENTOR(S) : JANOS ZERGENYI

It is certified that error appears in the above—identified patent and that said Letters Patent is hereby corrected as shown below:

Claim 1, Column 21, line 28 reads:

"mula I or R(+) configuration being converted into"

Should read:

-mula I of R(+) configuration being converted into-

Signed and Sealed this

Sixteenth Day of March 1982

[SEAL]

Attest:

*Attesting Officer*

GERALD J. MOSSINGHOFF

*Commissioner of Patents and Trademarks*